United States Patent
Almering et al.

(10) Patent No.: US 12,195,415 B2
(45) Date of Patent: Jan. 14, 2025

(54) PROCESS FOR THE EFFICIENT PRODUCTION OF BIO HIGH PURITY ISOBUTENE FROM RENEWABLES

(71) Applicant: LUMMUS TECHNOLOGY LLC, Houston, TX (US)

(72) Inventors: Martinus Johannes Almering, Houston, TX (US); Rosette Barias, Houston, TX (US); Todd Vogt, Houston, TX (US)

(73) Assignee: Lummus Technology LLC, Houston, TX (US)

( * ) Notice: Subject to any disclaimer, the term of this patent is extended or adjusted under 35 U.S.C. 154(b) by 0 days.

(21) Appl. No.: 18/167,758

(22) Filed: Feb. 10, 2023

(65) Prior Publication Data

US 2023/0250039 A1 Aug. 10, 2023

Related U.S. Application Data

(60) Provisional application No. 63/308,944, filed on Feb. 10, 2022.

(51) Int. Cl.
| | | |
|---|---|---|
| C07C 2/08 | (2006.01) | |
| C07C 1/24 | (2006.01) | |
| C07C 7/04 | (2006.01) | |

(52) U.S. Cl.
CPC ............... *C07C 2/08* (2013.01); *C07C 1/24* (2013.01); *C07C 7/04* (2013.01)

(58) Field of Classification Search
None
See application file for complete search history.

(56) References Cited

U.S. PATENT DOCUMENTS

| | | | | |
|---|---|---|---|---|
| 6,005,150 A | * | 12/1999 | Vora | C07C 41/06 |
| | | | | 585/329 |
| 9,840,676 B1 | * | 12/2017 | Harvey | C07C 2/24 |

(Continued)

OTHER PUBLICATIONS

Phillips et al. ("Production of Ethylene from Hydrous Ethanol on HZSM-5 under Mild Conditions", Ind. Eng. Chem. Res., 1997, 36, 4466-4475). (Year: 1997).*

(Continued)

*Primary Examiner* — Ali Z Fadhel
(74) *Attorney, Agent, or Firm* — Osha Bergman Watanabe & Burton LLP

(57) ABSTRACT

A process and system for converting bio ethanol to high purity isobutene is provided. The system includes a dehydration unit configured to receive a bio ethanol containing stream, convert the bio ethanol to bio ethylene, and produce a bio ethylene containing stream, a dimerization unit configured to receive the bio ethylene stream, dimerize ethylene, and produce an n-butenes containing stream, a skeletal isomerization unit configured to receive the n-butenes containing stream, convert n-butenes to produce a skeletal isomerization stream comprising an isobutene, isobutane, n-butenes, and n-butane, and a catalytic separation unit configured to receive the skeletal isomerization stream, convert olefins and/or isoolefins contained therein to produce a converted skeletal isomerization reaction product, and to fractionate the skeletal isomerization reaction product and produce bio isobutene.

22 Claims, 8 Drawing Sheets

(56) References Cited

U.S. PATENT DOCUMENTS

| | | | |
|---|---|---|---|
| 2008/0154078 A1* | 6/2008 | Bozzano | C07C 6/04 |
| | | | 422/600 |
| 2010/0174126 A1 | 7/2010 | Loescher | |
| 2013/0158321 A1 | 6/2013 | Olivier-Bourbigou et al. | |
| 2015/0247100 A1* | 9/2015 | Bradin | C10G 3/49 |
| | | | 585/254 |
| 2015/0251968 A1* | 9/2015 | Brianti | C07C 41/06 |
| | | | 585/639 |
| 2016/0368833 A1* | 12/2016 | Roza | C12P 5/026 |
| 2020/0062674 A1* | 2/2020 | Cao | C10G 69/06 |
| 2021/0300841 A1 | 9/2021 | Thotla et al. | |

OTHER PUBLICATIONS

Phillips, Cory B. et al. "Production of ethylene from hydrous ethanol on H-ZSM-5 under mild conditions." Industrial & Engineering Chemistry Research, 1997, vol. 36, No. 11, pp. 4466-4475 (10 pages).

Sun, Junming, et al. "Direct conversion of bio-ethanol to isobutene on nanosized ZnxZryOz mixed oxides with balanced acid-base sites." Journal of the American Chemical Society, 2011, vol. 133, pp. 11096-11099 (4 pages).

International Search Report issued in International Application No. PCT/US2023/012845 dated Jul. 17, 2023 (4 pages).

Written Opinion issued in International Application No. PCT/US2023/012845 dated Jul. 17, 2023 (6 pages).

\* cited by examiner

PROCESS FOR THE EFFICIENT PRODUCTION OF BIO HIGH PURITY ISOBUTENE FROM RENEWABLES

FIELD OF THE DISCLOSURE

Embodiments of the present disclosure generally relate to processes and systems for production of high purity isobutene from renewable feedstocks, such as bio-derived ethanol. Such reaction schemes may include dehydration, dimerization, skeletal isomerization, and reactive separation to attain the desired conversion of bio-derived ethanol to a high purity isobutene product.

BACKGROUND

High purity isobutene is a key component used in the manufacture of polymers used in a variety of applications such as tires and lubricants. High purity isobutene is a requirement for the manufacture of many of these polymer systems. However, production of high purity isobutene can be an energy intensive process that utilizes non-renewable feedstocks. Thus, there is a continuing need to make chemicals, such as high purity isobutene, from renewable sources, such as bio alcohols.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a system for converting bio ethanol to high purity isobutene. The system includes a dehydration unit configured to receive a bio ethanol containing stream, convert the bio ethanol to bio ethylene, and produce a bio ethylene containing stream, a dimerization unit configured to receive the bio ethylene stream, dimerize ethylene, and produce an n-butenes containing stream, a skeletal isomerization unit configured to receive the n-butenes containing stream, convert n-butenes to produce a skeletal isomerization stream comprising an isobutene, isobutane, n-butenes, and n-butane, and a catalytic separation unit configured to receive the skeletal isomerization stream, convert olefins and/or isoolefins contained therein to produce a converted skeletal isomerization reaction product, and to fractionate the skeletal isomerization reaction product to produce a bio isobutene product fraction.

In another aspect, embodiments disclosed herein relate to a method of producing high purity isobutene from bio ethanol. The method includes dehydrating bio ethanol to produce bio ethylene, dimerizing the bio ethylene to form n-butenes, skeletal isomerizing the n-butenes to form a bio C4 mixture comprising an isobutene, isobutane, n-butenes, and n-butane, and reacting and fractionating the bio C4 mixture to separate isobutene from unconverted n-butenes, and recovering the bio isobutene.

In another aspect, embodiments herein relate to a system for converting bio ethanol to high purity bio-isobutene. The system includes: a dehydration unit configured to receive a bio ethanol containing stream, convert the bio ethanol to bio ethylene, and produce a bio ethylene containing stream; a dimerization unit configured to receive the bio ethylene containing stream, dimerize the bio ethylene, and produce a bio n-butenes containing stream; an olefin skeletal isomerization unit configured to receive the bio n-butenes containing stream, convert n-butenes to produce a skeletal isomerization C4 olefin containing stream comprising isobutene and n-butenes. The system further includes, in some embodiments, a catalytic reaction/separation unit configured to: receive the skeletal isomerization C4 olefin containing stream, convert isobutene to one or more of methyl tert-butyl ether, ethyl tert-butyl ether, tertiary butyl alcohol and isobutyl alcohol, separate the n-butenes from the one or more of methyl tert-butyl ether, tertiary butyl alcohol and isobutyl alcohol, back crack the one or more of methyl tert-butyl ether, tertiary butyl alcohol and isobutyl alcohol to form isobutene and one or more of water and methanol, and separate the isobutene from the one or more of water and methanol to produce a bio isobutene product fraction. Alternatively, the catalytic reaction/separation unit is configured to: receive the skeletal isomerization C4 olefin containing stream; convert 1-butene contained in the n-butenes to 2-butenes; separate the 2-butenes from the isobutene to produce a 2-butenes fraction and a bio isobutene product fraction.

Other aspects and advantages of the claimed subject matter will be apparent from the following description and the appended claims.

DETAILED DESCRIPTION

Figure 1:
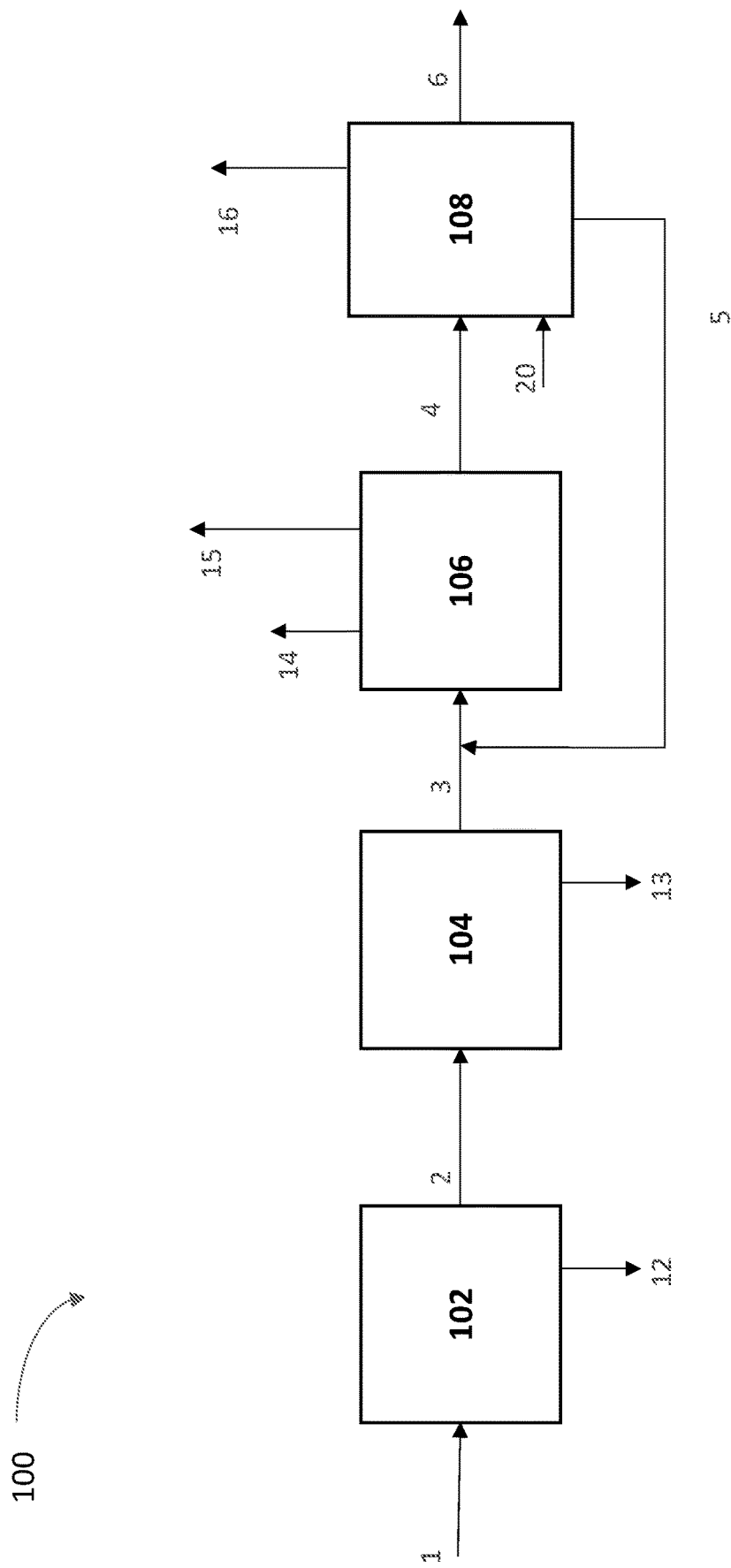
FIGS. 1 and 1A are block flow diagrams of a system for producing high purity bio-isobutene in accordance with one or more embodiments.

Embodiments disclosed herein are directed to processes and systems to produce high purity isobutene from bioethanol. For embodiments requiring proper "green" certification, all steps according to such embodiments may be proven on bio-based feedstocks or bio-based intermediates, and do not include any fossil-based feedstocks or intermediates.

In general, the process configuration of embodiments herein includes four primary unit operations. The first unit is an alcohol dehydration unit for producing ethylene. The alcohol dehydration unit may be used, for example, for the dehydration of a bio ethanol feedstock to form ethylene. Other alcohol and bio-alcohol feeds may also be used. The second unit is a dimerization unit for dimerization of ethylene to form n-butenes. The third unit is a skeletal isomerization unit that produces an isobutene/isobutane/n-butene mixture, and a small amount of C5+ byproduct is produced as well. In some embodiments, there may be little or no isobutane formed in the skeletal isomerization unit.

The fourth unit is a catalytic separation unit configured to receive the isobutene/isobutane/n-butane/n-butene mixture from the skeletal isomerization unit, convert components within the stream to form an easily separable mixture, and to recover a high purity isobutene (HPIB) product.

In one or more embodiments of the present disclosure the purity of the HPIB produced may be from a lower amount of any of 85%, 86%, 87%, 88%, or 89% on a wt % basis, to an upper limit of any of 90%, 91%, 92%, 93%, 94%, 95%, 98%, 98.5, 99.0, 99.5, 99.8 or 99.9% on a wt % basis.

In some embodiments, the catalytic separation unit may be a catalytic deisobutenizer to receive the isobutene/isobutane/n-butane/n-butene mixture and to concurrently fractionate the mixture while converting 1-butene to 2-butenes, to produce a high purity isobutene product and recover some unconverted n-butenes and n-butane. The n-butenes produced in the fourth unit may be recycled into the third unit to produce additional isobutene, while the n-butane may act as a diluent to help control the reaction within the skeletal isomerization unit. In some instances, such as when the formation of n-butane by-product is low, the resulting recycle back into the third unit would also have a low amount of n-butane, and a saturation (hydrogenation) step may be required to create n-butane for use as a diluent during skeletal isomerization.

In other embodiments, the catalytic separation unit may be an oxygenate/back-cracking separation unit. As an alternative to a catalytic separation unit including a catalytic deisobutenizer for separation of the C4s received from the skeletal isomerization unit, embodiments herein further contemplate feeding the skeletal isomerization C4s to a separation unit including an oxygenate reactor, a back-cracking reactor, and a separation system. The back-cracking separation units according to embodiments herein may receive a mixed stream, including the isobutene, from the skeletal isomerization unit, selectively react the isobutene with an oxygenate such as water, methanol, ethanol, propanol, or isobutanol to form an alcohol or ether (oxygenated intermediate) to facilitate separation of the isobutene (as an oxygenated isobutene intermediate) from the other C4 components in the mixture, and then back crack the oxygenated intermediate to recover the isobutene essentially free of the other C4 impurities, such as n-butenes and isobutane, as may be produced and recovered along with the dimerization and skeletal isomerization reactor effluents.

While described above with respect to four primary units, each unit may include reactors, heat exchangers, separators, feed treatment, internal recycles, and other processing or support equipment and features to achieve the desired conversion and products; while not all aspects of the unit operations are described in detail herein, one skilled in the art should appreciate the primary function of each respective unit based on the description herein.

A block flow diagram of a system 100 in accordance with one or more embodiments is show in FIG. 1. Compositional ranges for each of the streams associated with each of the following process steps according to some embodiments herein are shown in Table 1, below. In general, system 100 may include an alcohol dehydration unit 102, an ethylene dimerization unit 104, a skeletal olefin isomerization unit 106, and a separation unit 108.

The process may include a first step of dehydrating bio ethanol to form bio-ethylene. A bio-derived alcohol, such as a bio ethanol stream 1 may be fed to the ethanol dehydration unit 102. Ethanol dehydration unit 102 may include one or more reactors containing a catalyst for dehydrating ethanol (contained in feed stream 1) to produce ethylene (stream 2). Water and other impurities or byproducts may be withdrawn from the ethanol dehydration unit 102 via one or more flow streams 12.

After the ethanol is dehydrated, the process includes dimerization of the ethylene to form n-butenes. The bio-ethylene stream 2 recovered from the ethanol dehydration unit 102 may be fed to ethylene dimerization unit 104. Ethylene dimerization unit 104 may include one or more reactors containing a catalyst for dimerizing the bio-derived ethylene to form bio-derived butenes, which may include a mixture of both 1-butene and 2-butenes. The bio-derived butenes are recovered via flow stream 3, while C5 and heavier byproducts may be recovered from dimerization unit 104 via one or more flow streams 13.

Then, the process includes skeletal isomerization of the n-butenes to form a mixed C4 stream, which may be an isobutene/isobutane/n-butane/n-butene mixture. The bio-derived butenes stream 3 recovered from ethylene dimerization unit 104 may be fed to C4 skeletal olefin isomerization unit 106. C4 skeletal olefin isomerization unit 106 includes one or more reactors containing a catalyst for skeletal isomerization of the bio-derived butenes to form bio-derived isobutene. The reaction effluent, which may include unreacted n-butenes and isobutene, may be recovered via flow line 4, while C3 and lighter reaction byproducts may be recovered via flow line 13 and C5 and heavier byproducts may be recovered via flow line 14.

The final step includes reactive separation, such as catalytic deisobutenization, to fractionate isobutene from unconverted n-butenes and produce a high purity isobutene product. The bio-derived C4 reaction effluent (stream 4) may be fed along with hydrogen 20 to a catalytic deisobutenizer 108. The catalytic distillation unit contains one or more catalyst zones and distillation structure to concurrently positionally isomerize 1-butene to 2-butenes while fractionating the C4 mixture, producing a bottoms distillation product stream 5 containing 2-butenes and any n-butane, a vent gas stream 16, and a bio-derived isobutene product stream 6. Embodiments of the separation unit 108 (deisobutenization) may include an integrated isobutene stripper to remove trace isobutane from the high purity isobutene product. Any unconverted n-butenes (stream 5) may be recycled back into the skeletal isomerization unit 106 to produce additional isobutene (stream 4).

TABLE 1

| | Steam: | | | | | |
|---|---|---|---|---|---|---|
| Main Components: | 1 Range wt % | 2 Range wt % | 3 Range wt % | 4 Range wt % | 5 Range wt % | 6 Range wt % |
| Ethanol | 80-99.9 | | | | | |
| Ethylene | | 99-99.99 | | | | |
| n-butenes | | | 95-99.99 | 10-45 | 20-80 | |

TABLE 1-continued

| | Steam: | | | | | |
|---|---|---|---|---|---|---|
| Main Components: | 1 Range wt % | 2 Range wt % | 3 Range wt % | 4 Range wt % | 5 Range wt % | 6 Range wt % |
| isobutene | | | | 10-30 | 0-5 | 97-99.99 |
| n-butane | | | | 30-70 | 40-85 | |

Figure 1A:
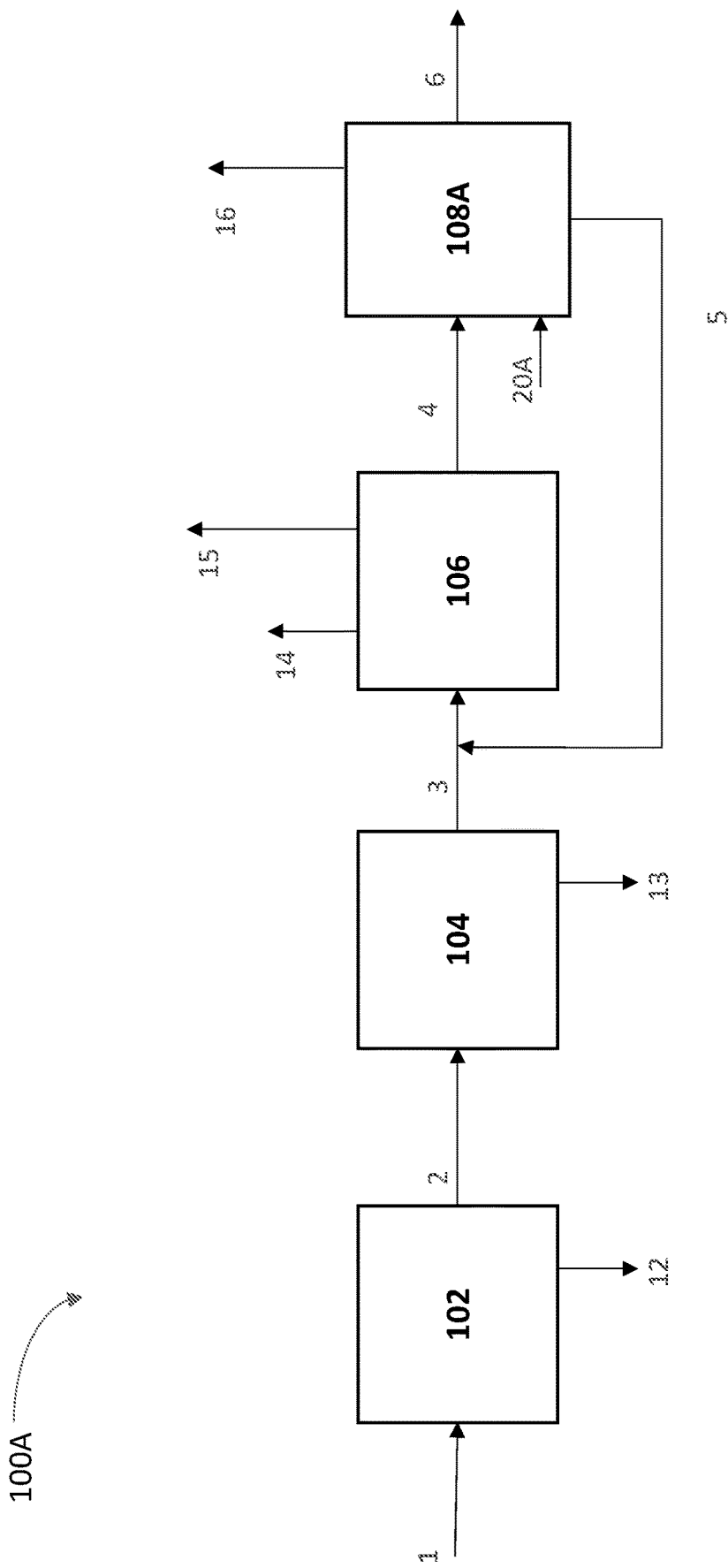

A block flow diagram of a system 100A in accordance with one or more embodiments is show in FIG. 1A. In general, system 100A may include an alcohol dehydration unit 102, an ethylene dimerization unit 104, a skeletal olefin isomerization unit 106, and a reactive separation unit 108A, where units 102, 104, and 106 are as described above with respect to FIG. 1. In this embodiment, the bio-derived C4 reaction effluent (stream 4) may be fed along with an oxygenate 20A, such as water, methanol, or ethanol, to separation unit 108A. Separation unit 108A includes internal process steps (not illustrated) to selectively react isobutene to form an alcohol or ether, recover the alcohol or ether, and then back crack the separated alcohol or ether to recover a high purity isobutene stream 6 and one or more byproduct streams 16. N-butenes, isobutane, or n-butane recovered in reactive separation unit 108 may be recycled to the skeletal isomerization unit 106, as noted above. Separation units 108 and 108A are further detailed below with respect to FIGS. 5 and 7.

Each of the four primary units according to embodiments herein include reactors (such as dehydration, dimerization, skeletal isomerization, reactive separation, as illustrated in FIGS. 1 and 1A). Reactors useful in embodiments disclosed herein may include traditional fixed bed reactors, boiling point reactors, and pulsed flow reactors, where the reactant flow and product flow may be co-current or counter-current. Boiling point and pulsed flow reactors may also provide for a continuous washing of the catalyst in addition to capturing at least a portion of the heat of reaction through evaporation, allowing for an improved reactor temperature profile as compared to conventional fixed bed reactors. Reactors useful in embodiments disclosed herein may be used as a stand-alone reactor or may be used in combination with one or more reactors of the same or different type.

Any type of reactor may be used to carry out the reactions described herein. The examples of reactors suitable for carrying out the reactions of embodiments herein may include distillation column reactors, divided wall distillation column reactors, traditional tubular fixed bed reactors, bubble column reactors, slurry reactors equipped with or without a distillation column, pulsed flow reactors, catalytic distillation columns wherein slurry solid catalysts flow down the column, conventional fixed bed reactors, or any combination of these reactors. Multiple-reactor systems useful in embodiments disclosed herein may include a series of the same type of reactor or reactors in parallel, or different types of reactors in series, for the respective reaction zones. A person of ordinary skill in the art would recognize that other types of reactors may also be used.

Bio Ethanol Dehydration Unit 102

Feeds to the dehydration system may comprise, consist essentially of, or consist of bio-derived ethanol. A fresh bio-derived ethanol feedstock may be provided from any number of sources. The bio-derived ethanol feedstock may be of a high purity, such as greater than 50 wt % bio-derived ethanol, greater than 70 wt % bio-derived ethanol, greater than 80 wt % bio-derived ethanol, greater than 90 wt % bio-derived ethanol, greater than 95 wt % bio-derived ethanol, or greater than 98 or 99 wt % bio-derived ethanol. In some embodiments, the remainder of the feedstock may include additional bio-derived hydrocarbons or inert diluents, such as nitrogen or paraffins.

Bio-derived ethanol feeds may be derived from fermentation processes, for example, such as the fermentation of renewable resources such as corn, corn stalks, corn cobs, lignocellulose, sugarcane, sugar beets, and wheat, among others. Other types of bio-derived ethanol may also be used. Various alcohol dehydration technologies and methods exists, known to those skilled in the art, and will not be expanded upon here other than to note that various reactor types, catalysts, and configurations may be used, and operating conditions may be appropriately selected based on the reaction type, catalyst, and overall feed composition to achieve the desired conversion of ethanol to ethylene. Dehydration of ethanol to form ethylene may be accomplished, for example, using the processes as described in U.S. Pat. No. 9,181,143 or U.S. Ser. No. 11/260,367, each to Braskem. Other known processes may also be used to dehydrate the bio-derived ethanol to form bio-derived ethylene according to embodiments herein.

Bio ethanol feeds useful in embodiments disclosed herein may contain impurities, such as water, among other impurities that may be present in a fermentation broth or other sources of the bio-derived ethanol. For example, bio ethanol feeds may contain a certain amount of water. Typically, the water is removed from the bio ethanol. However, as water is also a byproduct of the ethanol dehydration reaction, bio-derived ethanol feeds used in embodiments disclosed herein may include water as an impurity. Excessive water in the feed may decrease reactor conversion equilibrium, discussed below, and may result in increased reboiler duties, but water as a feed impurity may be tolerated in systems described herein.

In some embodiments, bio ethanol feeds may include some amount of water, such as up to 40 weight percent water; up to 30 weight percent water in other embodiments; up to 20 weight percent water in other embodiments; up to 10 weight percent water in other embodiments; up to 5 weight percent water in other embodiments; and up to 2 weight percent water in yet other embodiments. In other embodiments, bio ethanol feeds may be substantially pure ethanol. The amount of water that may be used within the catalytic reaction zones may depend on (1) the reaction equilibrium constant and (2) the enthalpy balance for conversion of ethanol to ethylene.

In the dehydration system, ethanol is dehydrated to produce ethylene by the removal of water from ethanol. This process typically involves heating the ethanol in the presence of an acidic catalyst which facilitates the breaking of the hydroxyl (—OH) group and the formation of a double bond between the carbon atoms. The resulting ethylene product can then be collected and used for the production of isobutene.

Dehydration reaction conditions may vary based on the feed mixture used. Dehydration temperatures may range from 30° C. to 500° C. in some embodiments. The dehydration reaction may be carried out under pressures in the range from 1 bar to 22 bar (0 psig to 300 psig) in some embodiments. The temperature and pressure used may depend upon the reactor type, reaction phase, and catalyst(s) employed for the reaction, and vary widely.

Contact of the ethanol with dehydration catalysts, at dehydration conditions as described herein, may result in the production of ethylene, unreacted alcohols, and heavies, which may include by-product ethers, alcohols, and oligomers, such as a dimer or trimer of the desired olefin product. In some embodiments, contact of a bio-derived ethanol feed with catalysts as described herein may result in conversion of at least 99 weight percent of the ethanol; at least 95 weight percent in other embodiments; at least 90 weight percent in other embodiments; at least 80 weight percent in other embodiments; and at least 70 weight percent in other embodiments.

The dehydration reaction effluent may then be fed to a separation system to separate the water and other reaction byproducts from the desired bio-ethylene product. The separation system may include membrane separation units, distillation units, extractive distillation units and other means for separating the water-ethylene mixture and for separation of other impurities so as to provide a high purity bio-ethylene product (high purity being greater than 95 wt %, greater than 98 wt %, greater than 99 wt %, greater than 99.5 wt %, or greater than 99.9 wt % in various embodiments). In some embodiments, the separation system may include a water scrubber, wash column, ethylene distillation column, and a stripper to recover a fairly pure ethylene product in the downstream dimerization step.

The exact configuration of the units and the process conditions used can vary depending on the specific process employed, catalyst used, production capacity, and product quality requirements. The dehydration process can also include internal recycle for unreacted ethanol.

Figure 2:
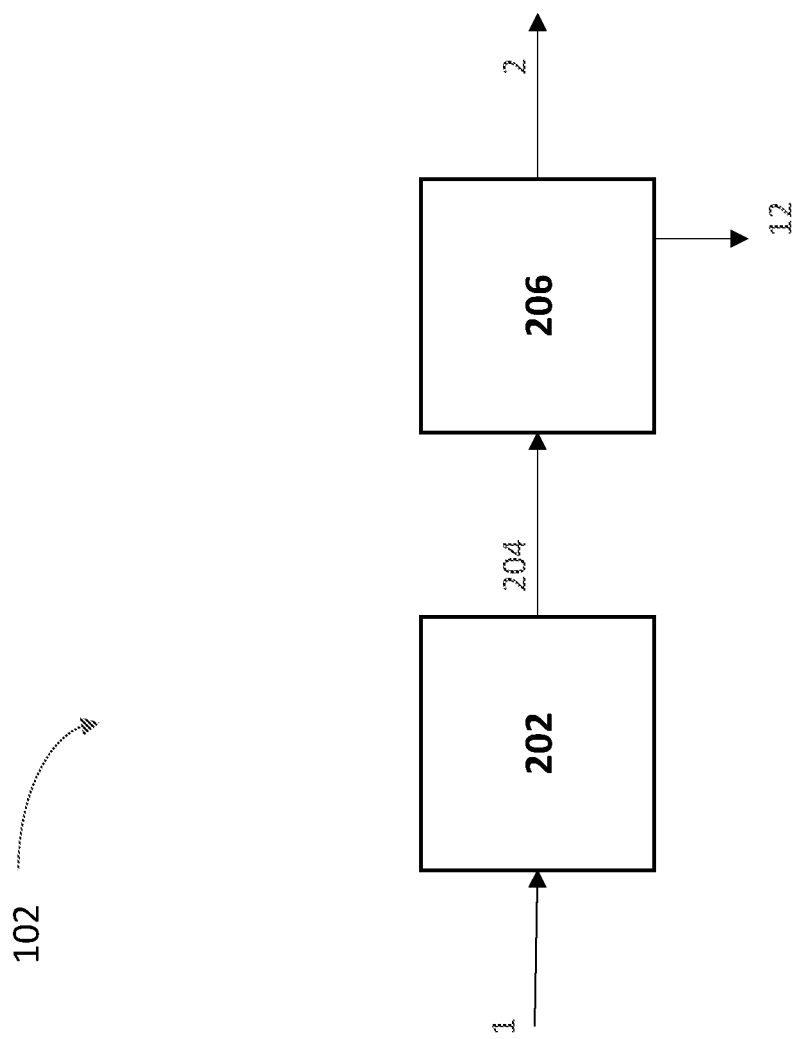
FIG. 2 is a block flow diagram of a bio ethanol dehydration unit in accordance with one or more embodiments.

A general process block flow diagram of alcohol dehydration units according to embodiments herein is illustrated in FIG. 2. A bio-derived alcohol, such as a bio ethanol stream 1 is fed to an ethanol dehydration reactor 202. Ethanol dehydration reactor 202 may contain a dehydration catalyst and be operated at conditions suitable for dehydrating ethanol (contained in feed stream 1) to produce ethylene and water. The dehydration reactor effluent is recovered from the dehydration reactor via flow stream 204, which is fed to separation unit 206 for separating the bio-ethylene product 2 from water and other impurities or byproducts recovered via one or more flow streams 12.

Bio-Ethylene Dimerization Unit 104

After the ethanol is dehydrated, the process includes dimerization of the ethylene to form n-butenes. Various catalysts and reactor configurations may be used for the selective dimerization of ethylene to form butenes. One example is the Lummus Ethylene Dimerization process, which may selectively dimerize ethylene to butenes, selectively forming 2-butenes to 1-butene at a ratio of about 9:1. Advantageously, producing a high ratio of 2-butenes to 1-butene may facilitate or ease requirements of downstream units, including the separation unit, in the production of a high purity isobutene stream having little or no 1-butene as an impurity. Another example of dimerization reactors is the ALPHABUTOL process (Axens) that uses a titanium-based catalyst for the dimerization of ethylene to butene. Other known processes may also be used to dimerize the bio-derived ethylene to form bio-derived butenes according to embodiments herein. Byproducts including C5 and heavier components, such as trimers, tetramers, or other oligomers, as well as byproducts resulting from reaction of ethylene with any reaction modifiers present may result in various C5 and heavier hydrocarbon species. Following dimerization of the ethylene to form bio-butenes, the reaction effluent may be fed to a separation system for separation of the desired C4 product stream from the C5 and heavier byproducts.

Figure 3:
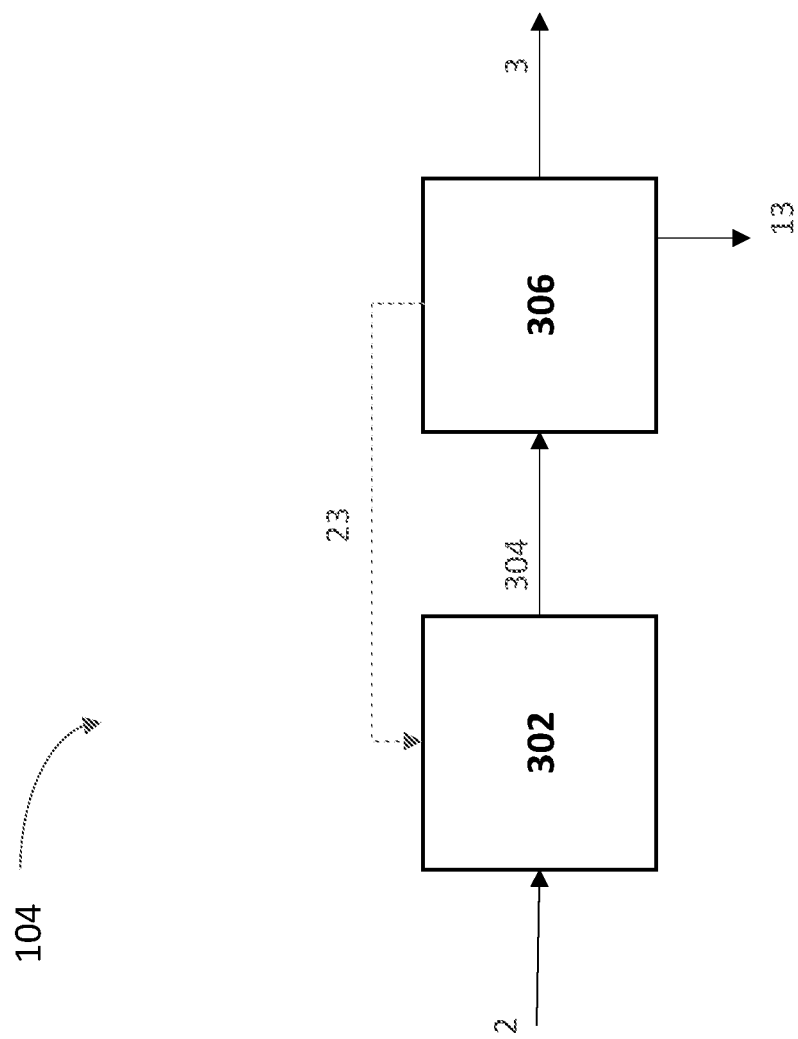
FIG. 3 is a block flow diagram of a bio-ethylene dimerization unit in accordance with one or more embodiments.

A general process block flow diagram of ethylene dimerization units according to embodiments herein is illustrated in FIG. 3. A bio-derived ethylene, such as a bio-ethylene stream 2 may be fed to an ethylene dimerization reactor 302. Ethylene dimerization reactor 302 may contain a selective dimerization catalyst and be operated at conditions suitable for dimerizing ethylene (contained in stream 2) to produce n-butenes and various byproducts. The ethylene dimerization reactor effluent may be recovered from the ethylene dimerization reactor via flow stream 304, which may be fed to separation unit 306 for separating the raw bio-butene product stream 3 from C5 and heavier impurities or byproducts recovered via one or more flow streams 13. In some embodiments, such as where ethylene conversion is incomplete, ethylene may be stripped from the butenes produced, and may be purged or recycled via flow line 23 to the dimerization reactors for continued conversion. Separation unit 306 may include, for example, one or multiple distillation or extractive distillation columns for performing the desired separations.

Olefin Skeletal Isomerization Unit 106

Feeds to the third unit (olefin skeletal isomerization) may include a mixed C4 stream or a mixed C4+ stream from the bio-ethylene dimerization unit. Depending on the feedstock to the bio-ethylene dimerization unit, and the overall conversion in the ethylene dimerization unit, a catalyst de-oiler may be present between the bio-ethylene dimerization unit and the olefin skeletal isomerization unit. The purpose of the catalyst de-oiler is to remove at least a portion of the undesired C5+ byproducts as well as to hydrogenate at least a portion of any byproduct 1,3-butadiene formed in the bio-ethylene dimerization unit. The catalytic de-oiler thus may serve to prepare the dimerization effluent for the skeletal isomerization unit.

Skeletal isomerization is the process of converting a straight-chain alkene into a branched-chain alkene, or vice versa. This reaction involves the rearrangement of the carbon-carbon double bonds within the molecule, resulting in a different molecular structure and physical properties.

The skeletal isomerization process typically involves the use of a catalyst, such as a transition metal catalyst, to facilitate the rearrangement of the carbon-carbon double bonds. The reaction conditions, such as temperature, pressure, and catalyst type and concentration, are carefully controlled to optimize the conversion and selectivity of the reaction.

In the skeletal isomerization unit, the C4 feeds, including the dimerization effluent and any recycled n-butenes from the catalytic separation unit are mixed and vaporized. The combined feed streams, or select feed streams, may be heated, such as via a reactor feed/effluent heat exchanger, and then further heated to reaction temperature and sent to the isomerization reactors.

The skeletal isomerization of linear butenes (1-butene and 2-butenes) to isobutene may be performed in a vapor phase reactor over an olefin skeletal isomerization catalyst. Various skeletal isomerization technologies and methods exists, and many use an acidic catalyst. Olefin skeletal isomerization processes are known to those skilled in the art and will not be expanded upon here other than to note that various reactor types, catalysts, and configurations may be used, and operating conditions may be appropriately selected based on the reaction type, catalyst, and overall feed composition to achieve the desired conversion of normal butenes to isobutene.

In some embodiments, the skeletal isomerization reactor may use an acidic catalyst and operate at a temperature range of 250 to 450° C. where the chemical equilibrium provides enough drive towards n-butenes. These methods also operate between 1.0 bara and 2.5 bara. Embodiments herein may also use a dilution medium, provided from the downstream catalytic separation unit, to lower the partial pressure of the olefin in order to limit dimerization and thus improve selectivity. The resulting ratio of n-butenes to isobutene in the reactor effluent may be between 0.70 and 1.2.

The resulting reaction effluent, including the residual 1-butene, 2-butenes, isobutene, and any butanes (i.e., n-butane and isobutane), may be lean in 1-butene. For example, depending upon the severity of the reaction conditions used, the product may contain less than 1 wt % total of 1-butene, less than 0.5 wt % total in other embodiments; less than 0.1 wt % total in other embodiments; and less than 500 ppm total in yet other embodiments.

The effluent from the skeletal isomerization reactors may then be separated to recover a mixed C4 stream, including unreacted normal butenes (1-butene and 2-butenes), and isobutene. The recovered C4 stream may include lighter hydrocarbon byproducts in some embodiments. The reactions may also produce a fraction including C5 and heavier hydrocarbon byproducts. The isomerization reaction effluent in such embodiments may be separated within the third unit to produce a C5+ fraction, the C4 fraction, and a lights fraction, as illustrated in FIG. 1 and described above. The C5+ byproducts may be recovered as a fuel fraction or gasoline blending fraction in some embodiments. The C4 effluent from the isomerization reaction zone may then be fed to the fourth unit, the catalytic deisobutenizer.

Figure 4:
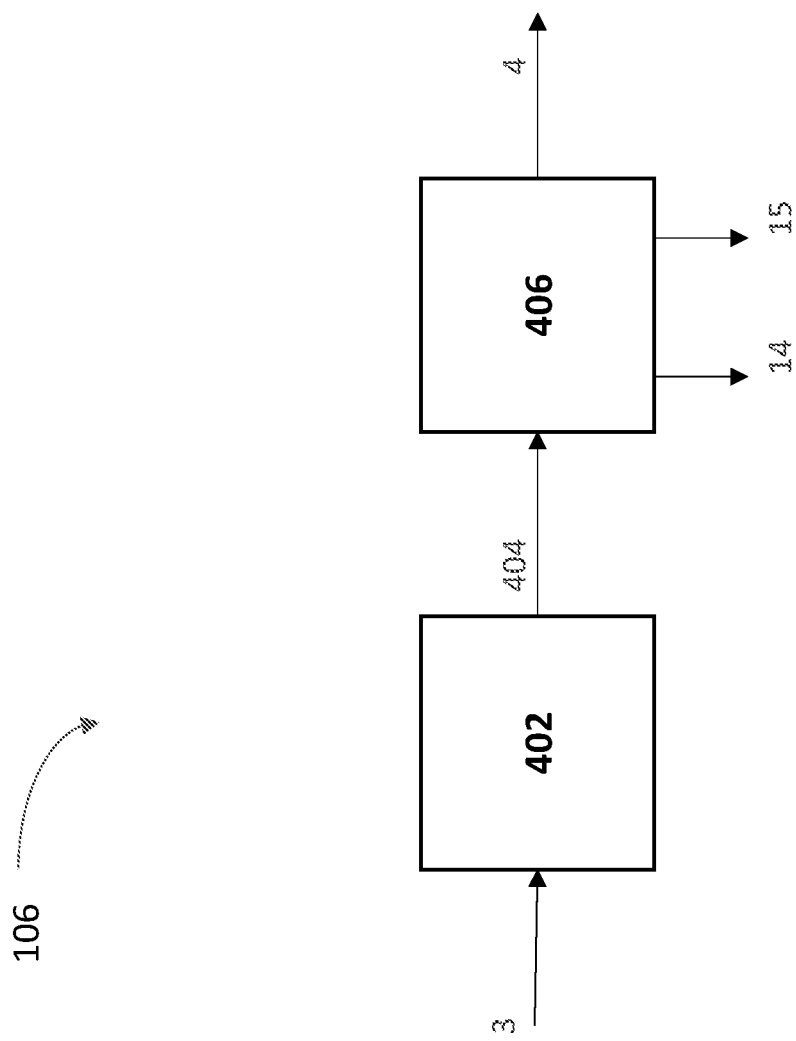
FIG. 4 is a block flow diagram of a bio-olefin skeletal isomerization unit in accordance with one or more embodiments.

A general process block flow diagram of olefin skeletal isomerization units according to embodiments herein is illustrated in FIG. 4. The bio-derived butenes, such as a bio-derived C4 stream 3 may be fed to an olefin skeletal isomerization reactor 402. Olefin skeletal isomerization reactor 402 may contain a skeletal isomerization catalyst and be operated at conditions suitable for skeletal isomerization of normal butenes (contained in feed stream 3) to produce isobutene. C3 and lighter byproducts, as well as C5 and heavier byproducts may also be produced. The skeletal isomerization reactor effluent may be recovered from the olefin skeletal isomerization reactor via flow stream 404, which may then be fed to separation unit 406 for separating the bio-derived C4 stream 4 from light byproducts, recovered via one or more flow Xstreams 14, and C5 and heavier byproducts, recovered via one or more flow streams 15.

Separation system 406 may include multiple distillation columns in some embodiments. For example, a depropanizer may be used to remove C3 and lighter components from the C4+ hydrocarbons in the skeletal isomerization reaction effluent, while a debutanizer may be used to recover the C4 stream (including the bio-derived butenes and isobutene) from the C5 and heavier byproducts. Other various configurations may be used to recover one or multiple lighter or heavier fractions. The C5+ byproducts may be recovered as a fuel fraction or gasoline blending fraction in some embodiments. The isobutene-containing product from the skeletal isomerization unit is then fed to the fourth unit, the catalytic separation unit.

Catalytic Separation Unit: Catalytic Deisobutenizer Unit 108

As described above, the final step includes reactive (catalytic) separation, some embodiments of which include catalytic deisobutenization to fractionate isobutene from unconverted n-butenes and produce a high purity isobutene product.

Figure 5:
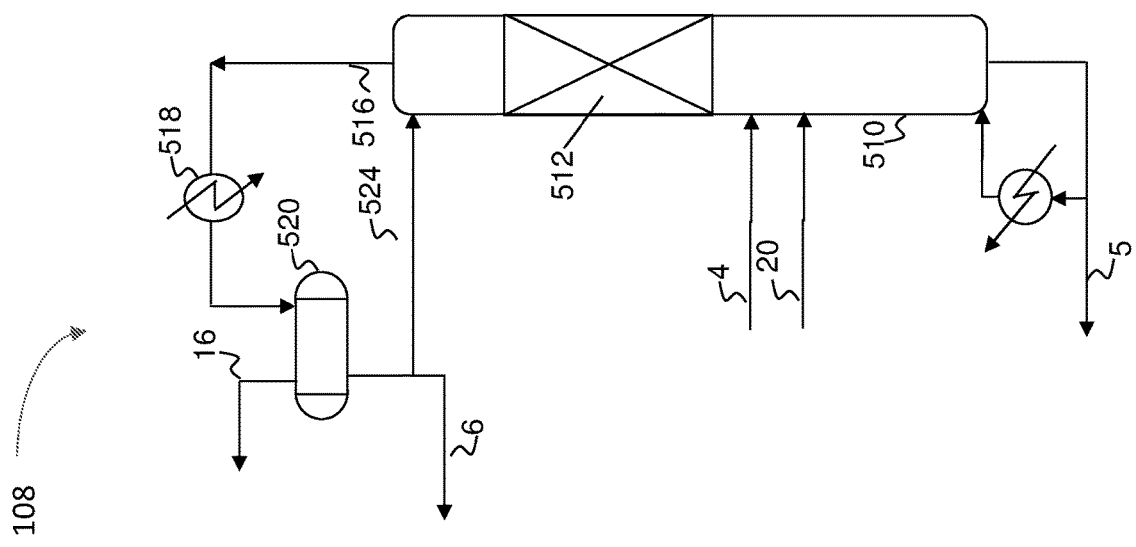
FIG. 5 is a simplified flow diagram of a catalytic deisobutenizer in accordance with one or more embodiments.

Referring now to FIG. 5, a simplified process flow diagram of catalytic deisobutenizer unit according to embodiments herein is illustrated. The initial step is feeding a mixed C4 stream 4, such as the mixed C4 reaction effluent from the olefin skeletal isomerization unit 106, to a deisobutenizer (catalytic distillation column) 510. In the catalytic distillation column 510, the mixed C4 stream containing 1-butene, isobutene and n-butane, among other C4 components, is fed to catalytic distillation column 510 near the bottom of a catalytic distillation section 512 (catalyst zone 512), which contains a supported hydroisomerization catalyst in the form of a catalytic distillation structure. Hydrogen may be fed via flow line 20, also introduced below the catalyst zone 12.

As the reactant feed contacts the catalyst, any butadiene in the feed is hydrogenated to butenes and equilibrium amounts of 1-butene and 2-butenes are produced at the catalyst. The 2-butenes is distilled away and taken as bottoms, driving the reaction at the catalyst sites toward the production of 2-butenes.

The stripping section of the column may contain a conventional distillation structure, such as bubble cap, sieve trays or inert packing, to allow for complete separation of the 2-butenes product from the lower boiling isobutene and isobutane. Any normal butane present will also be removed as bottoms. The 2-butenes and normal butane may then be recovered from the catalytic distillation column 510 via flow line 5.

Overhead stream 516, including isobutene and any isobutane, is condensed in condenser 518. The condensed overheads are collected in receiver separator 520, wherein the liquid isobutene and isobutane are separated from hydrogen and light materials which are vented via flow line 16. The hydrogen may be recycled to the catalytic distillation column 510 if desired (recovery and recycle of hydrogen not illustrated). A portion of the condensed overhead product is recycled via flow line 524 to the catalytic distillation column 510 as reflux. The isobutene and isobutane are removed as overheads product via flow line 6.

The overheads product stream 6 may include isobutene as well as isobutane as may result from byproduct hydrogenation within the catalytic distillation column 510 or as a reaction byproduct elsewhere in the overall system 100. In some embodiments, such as where a higher purity isobutene product is desired, overheads product stream 6 may be fed to a splitter (not illustrated) for separation of the isobutene from the isobutane. A small stripper may be required for trace isobutane removal, for example. In some embodiments, the deisobutenizer may be as described in U.S. Pat. No. 6,242,661 or U.S. Pat. No. 7,982,086. In other embodiments, an integrated isobutene (IB) stripper, such as that described in U.S. Ser. No. 11/053,177, may be used to remove isobutane from the isobutene, producing a higher purity bio-derived isobutene product.

The catalytic material employed for the isomerization reaction is preferably in a form to serve as distillation packing in such conventional distillation packing shapes as Raschig rings, Pall rings, saddles or the like and as such other structures as, for example, balls, irregular, sheets, tubes, spirals, packed in bags or other structures (such as those described in U.S. Pat. Nos. 4,242,530, 4,443,559, 5,189,001, 5,348,710, and 5,431,890), plated on grills or screens, or reticulated polymer foams (the cellular structure of the foams must be sufficiently large so as to not cause high pressure drops through the column, or otherwise arranged such as in chunks or concentration tubes to allow vapor flow). Similarly, the catalyst may be employed as palladium, platinum, or nickel supported on one-eighth inch alumina extrudates, either in bags or loosely packed in the column. In some embodiments, the catalyst may be contained in a structure as disclosed in U.S. Pat. Nos. 5,730,843, 5,266,546, 4,731,229, and 5,073,236.

The catalyst contained in the reaction zone of the catalytic distillation column may be any catalyst suitable for the isomerization or hydroisomerization of 1-butene to 2-butenes. In some embodiments, the catalyst may contain palladium, platinum, or nickel, and may be in the form of an extrudate, for example. For hydroisomerization, the hydrogen rate to the distillation column reactor should be sufficient to maintain the catalyst in the active (hydride) form, as hydrogen is lost from the catalyst by hydrogenation when butadiene is contained in the feed. The hydrogen rate may be adjusted such that there is sufficient hydrogen to support the butadiene hydrogenation reaction and replace hydrogen lost from the catalyst but kept below that required for hydrogenation of butenes or to cause flooding of the column. Generally, the mole ratio of hydrogen to C4 hydrocarbon fed to the bed of catalytic distillation column will be in the range from about 0.01:1 to 0.60:1, preferably 0.01:1 to 0.10:1.

Embodiments herein may perform the catalytic distillation step in a catalyst packed column which can be appreciated to contain a vapor phase and some liquid phase, as in any distillation. Because the reaction is occurring concurrently with distillation, the initial reaction products are removed from the reaction zone as quickly as possible. Further, as all the components are boiling, the temperature of reaction is controlled by the boiling point of the mixture at the system pressure, which may vary from tray to tray. The heat of reaction simply creates more boil up but no increase in temperature. Additionally, the reaction has an increased driving force because the reaction products have been removed and cannot contribute to a reverse reaction. As a result, a great deal of control over the rate of reaction and distribution of products can be achieved by regulating the system pressure. Also, adjusting the throughput (residence time=liquid hourly space velocity$^{-1}$) gives further control of product distribution and degree of 1-butene to 2-butenes conversion.

The temperature in the distillation column reactor is determined by the boiling point of the liquid mixture present at any given pressure. The temperature in the lower portions of the column will reflect the constitution of the material in that part of the column, and will be a higher temperature than the overhead; that is, at constant pressure a change in the temperature of the system indicates a change in the composition in the column. To change the temperature, the pressure is changed. Temperature control in the reaction zone is thus effected by a change in pressure; by increasing the pressure, the temperature in the system is increased, and vice versa.

The catalytic distillation column according to embodiments herein may be operated at an overhead temperature in the range of 32° C. to 138° C. and at pressures in the range of 3 bara to 20 bara, bearing in mind the effect of pressure on temperature as discussed above. In other embodiments, the catalytic distillation column according to embodiments herein may be operated at an overhead temperature in the range of 85° C. or 90° C. to 130° C. or 135° C. and at pressures in the range of 9 bara, 10 bara, or 11 bara to 16 bara, 18 bara, or 20 bara, where any lower limit may be combined with any upper limit. In other embodiments, the overhead temperature of the catalytic distillation column may be in the range from 32° C. to about 80° C., such as from about 47° C. to about 68° C., or from about 60° C. to about 65° C. In yet other embodiments, the overhead temperature may be in the range from a lower limit of 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 85 or 90° C. to an upper limit of 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 85, 90, 100, 110, 120, 130, or 138° C., where any lower limit may be combined with any upper limit. In some embodiments, the overhead pressure of the catalytic distillation column may be in the range from about 3 bara to about 12 bara, such as in the range from about 7 bara to about 10 bara. In yet other embodiments, the overhead pressure of the catalytic distillation column may be in the range from a lower limit of about 9, 10, 11, 12, 13, 14, or 15 bara to an upper limit of about 14, 15, 16, 17, 18, 19, or 20 bara. Bottoms temperatures of the catalytic distillation column will correspond to the boiling point of the higher boiling components at the operating conditions, and in various embodiments, may be in the range from about 60° C. to about 180° C., such as from about 60° C. to about 100° C., or from about 65° C. to about 88° C., for example, but may also be higher based on the desired overhead temperature and pressure. The temperature of operation may also take into consideration the activity of the catalyst for promoting the desired 1-butene to 2-butenes reaction.

In embodiments herein, the catalytic distillation column is operated under conditions, particularly temperature and pressure, which tend to exclude 2-butenes from contact with the catalyst while holding the 1-butene in contact with the catalyst. Thus, as 1-butene is isomerized to 2-butenes, it drops down in the column away from the catalyst and is removed as bottoms. The column may include a reflux, where the reflux ratio may be in the range from 0.5:1 to 33:1, for example.

As described above, the mixed C4s from the olefin skeletal isomerization reaction zone are fed to a catalytic distillation column. In the catalytic distillation column, the C4 stream is further processed using positional isomerization and hydrogenation catalysts, along with a hydrogen feed, converting 1-butene to 2-butenes and selectively hydrogenating any butadiene that may be present from upstream processing in the dehydration and skeletal isomerization units. Concurrent fractionation results in two C4 product streams in some embodiments, including a 2-butenes and n-butane bottoms product and a high purity isobutene overhead product. A hydrogen containing vent gas may also be recovered.

Isobutene product streams produced from processing of the skeletal isomerization mixed C4 effluent through a catalytic distillation column may have an isobutene content of at least 80 wt %. High purity isobutene product streams may be produced, having a purity of at least 85 wt %, at least 90 wt %, at least 95 wt %, at least 98 wt %, at least 99 wt %, at least 99.5 wt %, or at least 99.9 wt % in various embodiments.

In still other embodiments, catalytic distillation column herein may result in three C4-product streams, including a 2-butenes and n-butane bottoms product, an isobutane overhead product, and a high purity isobutene product. The high purity isobutene product may be recovered, for example, as a bottoms draw from a splitter, as noted above, or in some embodiments may be recovered as a side draw fraction from the catalytic distillation column. The side draw may be located within the column at an appropriate elevation to recover an isobutane/isobutene stream having a ratio of isobutane to isobutene in the range from 0.001:1 to 2:1, such as 0.01:1 to 1:1.5, or from 0.1:1 to 1:1 for example. The side draw may be located above the catalytic distillation reaction zone, and the feed may be located below the catalytic distillation reaction zone, providing for a side draw containing a relatively low amount of n-butenes, such that a stream containing greater than 80%, greater than 95%, greater than 98%, or greater than 99%, or greater than 99.9% isobutene may be recovered. Sufficient trays and height to the column may also be provided to result in an isobutane overhead stream containing primarily isobutane, such as greater than 95% or greater than 98% isobutane (each in wt %).

In some embodiments, due to the low make of 1-butene within the preceding units coupled with the isomerization of 1-butene to 2-butene within the catalytic distillation column, isobutene product streams produced herein, whether an overhead or a side draw from the catalytic distillation column, may have a purity of at least 99.9 wt %, 99.95 wt %, or 99.99 wt % isobutene based on a total amount of isobutene and 1-butene contained in the high purity isobutene product stream.

Figure 6:
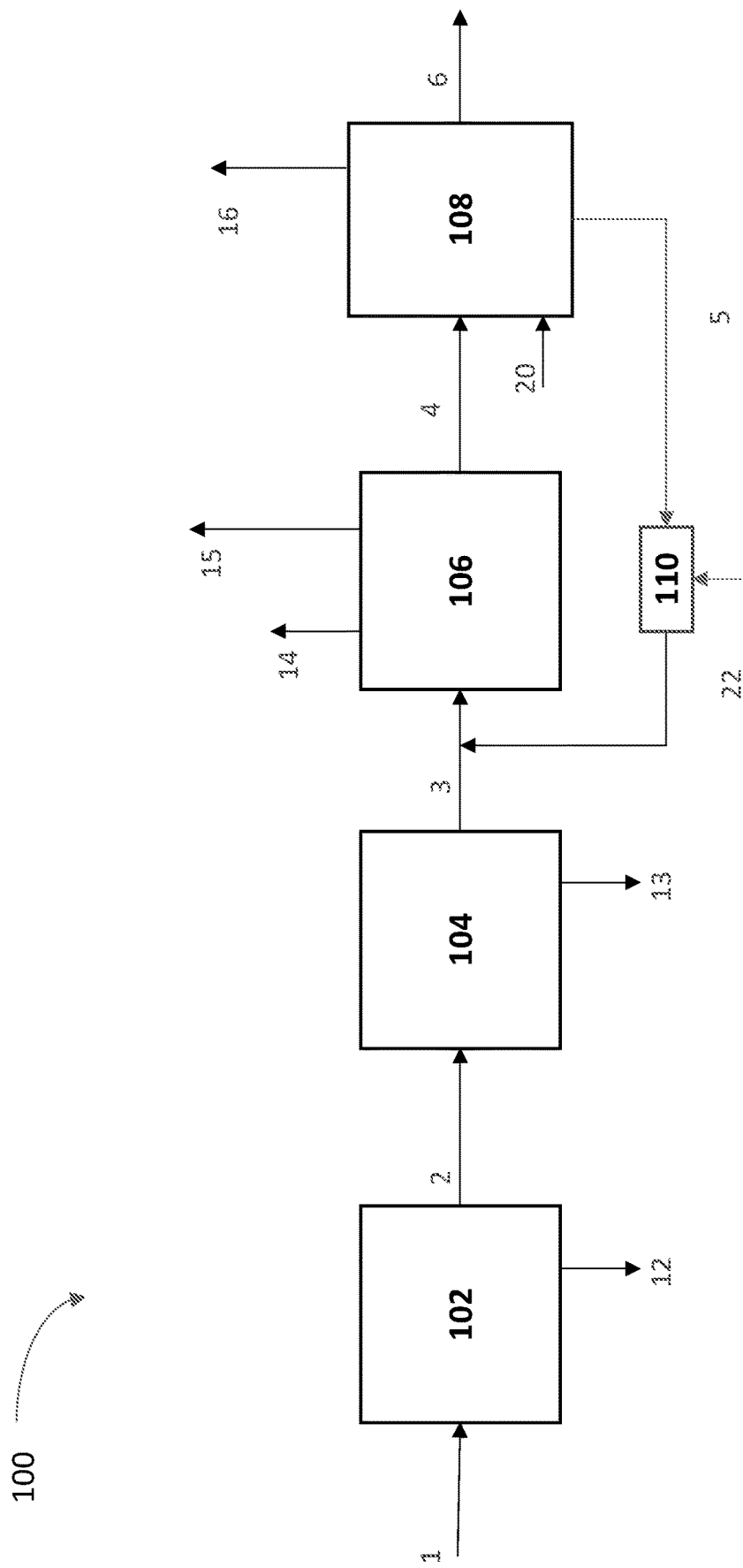
FIG. 6 is a block flow diagram of a system for producing high purity bio-isobutene in accordance with one or more embodiments.

It has been found that operation of the skeletal isomerization unit is improved with addition of diluent. The n-butenes produced in the catalytic distillation column unit may be recycled into the third unit (olefin skeletal isomerization) to produce additional isobutene, while the n-butane may act as a diluent to help control the reaction within the skeletal isomerization unit. In some instances, such as in embodiments where the formation of n-butane by-product is low, the resulting recycle back into the third unit would also have a low amount of n-butane. In such embodiments, and as illustrated in FIG. 6, a saturation (hydrogenation) reactor 110 may be used to react n-butenes with hydrogen 22 to form a desired amount of n-butane for use as a diluent during skeletal isomerization.

If present at sufficient quantities, the isobutane product may be dehydrogenated to form additional isobutene and hydrogen, if desired. The hydrogen may be recovered and used as a feed to the catalytic distillation column or the hydrogenation reactor to generate n-butane diluent, while the C4 dehydrogenation effluent may be fed to the catalytic distillation column, the isobutene stripper, or otherwise processed to recover the additional bio-derived isobutene.

Catalytic Separation: Oxygenate—Back-cracking Separation System 108A

The oxygenate—back-cracking separation system produces a high purity isobutene product stream by selectively converting the isobutene in the skeletal isomerization mixed C4 product stream to one or more of methyl tert-butyl ether (MTBE), ethyl tert-butyl ether (ETBE) tertiary butyl alcohol (TBA), butyl-butyl ether, or isobutyl alcohol, among other possible oxygenated intermediates, separating the resulting ether or alcohol from the lighter C4 n-olefins and paraffins, and then back-cracking the ether or olefin to form the constituent isobutene and water or alcohol, so that the isobutene can be easily separated from the water or alcohol and recovered as a high purity isobutene product stream. The recovered alcohol or water may then be fed back into the reactor for selectively converting the isobutene.

The reaction system may include one or more reactors and catalytic distillation reactors suitable for etherification of the isobutene and one or more alcohols to form one or more $C_4$ ethers, such as MTBE and/or ETBE. Alternatively, water may be used to convert the isobutene to an alcohol, such as TBA or isobutyl alcohol.

The $C_4$ isoolefins may be processed according to embodiments herein to etherify or alcoholify the isoolefins. Catalysts used in reactors and distillation column reactors according to embodiments herein may have functionality to selectively hydrogenate butadiene, isomerize olefins, as well as to etherify or alcoholify the isoolefins.

Typical conditions for the oxygenate reactions include catalyst bed temperatures above about 60° C. For catalytic distillation reactors, overhead pressures of above about 5.5 barg and equivalent liquid hourly space velocities of about 1.0 to 2.0 $hr^{-1}$ may be used. The temperature in the column is determined by the boiling point of the liquid mixture present at any given pressure. The temperature in the lower portions of the column will reflect the constitution of the material in that portion of the column, which will be higher than the overhead; that is, at constant pressure a change in the temperature indicates a change in the composition in the column. To change the temperature, the pressure in the column may be changed. Temperature control in the reaction zone is thus controlled by the pressure with the addition of heat (the reactions being exothermic) only causing more boil up. By increasing the pressure the temperature is increased, and vice versa. Even though a distillation column reactor is used, some of the isoolefin may be unconverted and may exit the column with the overheads.

The ether product, being the highest boiling material, is removed from the distillation column reactor as a bottoms, along with any dimers in the effluent from the upstream reactors. The overheads may contain unreacted light alcohols, such as ethanol used in the upstream reactors and/or a reactant in the distillation column reactor, and isoolefin along with light inerts, such as normal butenes and butanes.

The catalyst for the etherification may be any of known etherification catalysts such as an acidic cation exchange resin such as Amberlyst 15 as supplied by DuPont Chemical Company. A suitable catalytic structure may be used herein to place the cation exchange resin particles into a bed within the fixed bed reactor. Further, the temperatures and pressures may be similar to those known in the art for performing the specified reactions.

In some embodiments, the oxygenate reaction system may include an unreacted n-butenes effluent. The effluent containing unreacted n-butenes from the oxygenate reaction unit may be fed to a $C_4$ separation system. The $C_4$ separation system may be used to produce a 1-butene product stream and 2-butenes recycle stream. The 2-butenes recycle stream may feed the separated 2-butenes back to the skeletal isomerization system. In some embodiments, the etherification reaction system may produce an ETBE product stream.

The oxygenated (ether or alcohol) effluent from the etherification reaction system is then fed to a back-cracking unit.

The back-cracking system produces high purity isobutene, along with unreacted feed components and reaction byproducts, such as n-butenes, tert-butyl alcohol (TBA), ethanol, unconverted MTBE, ETBE and ethyl sec-butyl ther (ESBE), diethyl ether (DEE), dimethyl ether (DME), diisobutene (DIB), or butyl-butyl ether (BBE). The back-cracking unit includes distillation units that separate the components in the reaction effluent to give high purity isobutene. The recovered alcohol or water may be fed back to the oxygenate reaction system. In some embodiments, such as where the oxygenate is bio ethanol, the recovered ethanol may be fed back to the oxygenate reaction system to reduce the bio-derived ethanol make-up from the renewable source. No additional external ethanol feed is required in such embodiments.

Contact of the ether feed with catalysts as described herein, at decomposition conditions, may result in the production of the desired olefin and alcohols, and byproducts, which may include by-product ethers, alcohols, and oligomers, such as a dimer or trimer of the desired olefin product. In some embodiments, contact of an ether feed with catalysts as described herein may result in conversion of at least 90 wt % of the ether; at least 85 wt % in other embodiments; at least 80 wt % in other embodiments; at least 75 wt % in other embodiments; and at least 70 wt % in other embodiments.

Figure 7:
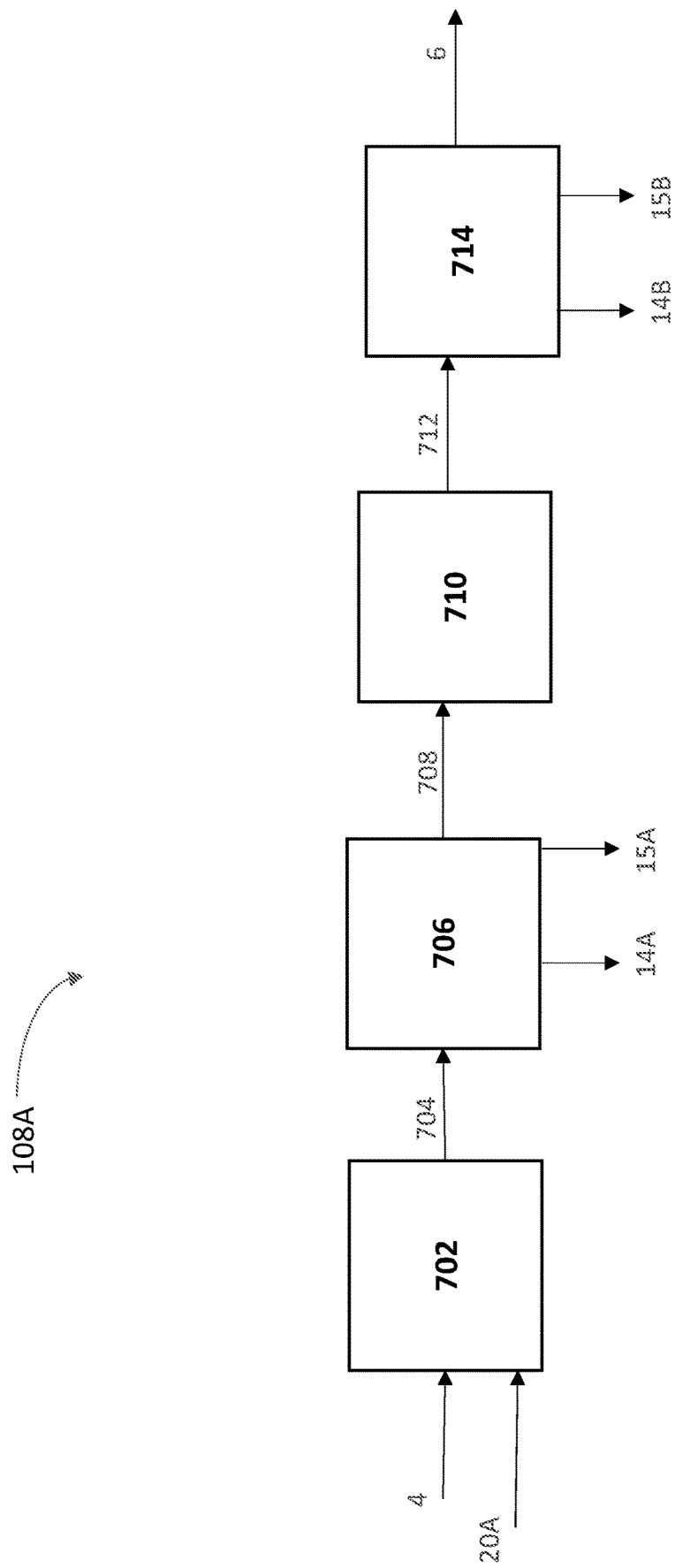
FIG. 7 is a block flow diagram of a separation system useful for producing high purity bio-isobutene in accordance with one or more embodiments.

Referring now to FIG. 7, a simplified block flow diagram of an oxygenate—back-cracking separation system 108A according to embodiments herein is illustrated. A bio derived mixed C4 stream 4, including isobutene among other components as described above, and a stream 20A containing an oxygenate reactant, such as methanol, ethanol, isobutanol, water, or a mixture thereof, may be fed to an etherification reaction system 702. Etherification reaction system 702 may include one or more reactors for selectively reacting, over an appropriate catalyst, the isobutene with the water, methanol, or ethanol to form one or more of MTBE, ETBE, TBA, butyl-butyl ether or isobutyl alcohol. The reaction effluent 704 may then be fed to a separation system 706, which may include one or more distillation columns or extractive distillation columns, to separate the MTBE, ETBE, TBA, butyl-butyl ether or isobutyl alcohol from the unreacted C4 components in the mixed feed stream 4, recovering the MTBE, ETBE, TBA, butyl-butyl ether or isobutyl alcohol as effluent stream 708, and recovering the lighter C4 components via one or more flow streams 14A. Unreacted water or alcohol and other etherification reaction byproducts may be recovered by one or more flow streams 15A.

The effluent stream 708 may then be fed to a back-cracking reaction system 710 for conversion of the MTBE, ETBE, TBA, butyl-butyl ether, or isobutyl alcohol back to the constituent molecules, isobutene and water, methanol, or ethanol. Back-cracking reaction system 710 may include one or more reactors containing an appropriate back-cracking catalyst. Back cracked effluent 712 may then be recovered from the reactors and fed to separation system 714, which may include one or more distillation or extractive distillation columns for recovering a high purity isobutene product 6, any heavy reaction byproducts 14B, and the alcohol or water reactant 15B, which can be recycled upstream to reaction system 702, if desired. While not illustrated, embodiments herein contemplate recovery of 1-butene, 2-butenes, MTBE, ETBE, or other components as a separate product stream from the various reaction effluents and separation schemes described above.

As described briefly above, embodiments may provide for the use of renewable feedstocks, and such renewable feedstocks may include bio ethanol or bio isobutanol, as may be derived from fermentation processes or from bio ethanol and the bio isobutene produced within the process schemes outlined above. Thus, embodiments herein may internally produce feedstocks used for the etherification reactions, facilitating use of bio derived feedstocks to produce fully certifiable bio derived products.

Because the formation of the alcohol or the ether provides for efficient separation of the isobutene from the n-butenes and isobutane that may be contained in the C4 skeletal isomerization product stream, separation zone 108A may be used to produce a high purity isobutene product similar to those as described above for unit 108.

Examples

In an exemplary prophetic embodiment, 400 KTA of bio ethanol is fed into the first unit and dehydrated. 162 KTA of by-products including water are produced and 239 KTA of bio-ethylene is produced. The bio-ethylene is dimerized in the second unit to form 12 KTA of C5+ by-products while 226 KTA of n-butenes is produced. During skeletal isomerization 3 KTA of a C3 purge is lost and 31 KTA of C5+ by-products are made while 994 KTA of n-butenes, isobutene and n-butane are produced. During catalytic distillation, 9 KTA of hydrogen and purge gases are lost while 183 KTA of high purity bio isobutene is isolated. 802 KTA of 2-butenes (288 KTA) and n-butane (514 KTA) are recycled back into the skeletal isomerization step.

Bio based polymers and elastomer are expected to be high value products. For proper green certification it is often required to demonstrate that all steps are proven on bio based intermediates rather than on fossil based intermediates even though the compositions between fossil and bio-based intermediates are similar. This Bio HPIB route allows manufacturers to make many products green, such as tires and lubricants. This route is unique since it uses readily available bio sourced ethanol for HPIB production at high yields with minimal by product formation without the production of isobutane which normally makes the production of HPIB process intensive.

Unique features of the present application may include using the ethylene dimer route in the process to make high purity bio isobutene. The recycle from the catalytic distillation column (CDDeIB) back to the isomerization unit allows for a build up of n-butane diluent necessary for the isomplus process: This is required to be able to use the dimer effluent. Because there is almost no production of isobutane (the paraffin) in the processes, a downstream IB stripper is small.

Embodiments of the present disclosure may provide at least one of the following advantages. The disclosed method may provide advantages over conventional methods of producing high purity isobutene because there is very little production of the paraffin isobutane, which requires energy intensive processes to convert to isobutene. Additionally, recycling unconverted n-butenes plus n-butane diluent back into the skeletal isomerization step allows for the n-butenes and n-butane to build up efficiently for the skeletal isomerization step to continue.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims

What is claimed:
1. A system for converting bio ethanol to high purity bio-isobutene, the system comprising:
 a dehydration unit configured to receive a bio ethanol containing stream, convert the bio ethanol to bio ethylene, and produce a bio ethylene containing stream;

a dimerization unit configured to receive the bio ethylene containing stream, dimerize the bio ethylene, and produce a bio n-butenes containing stream;

an olefin skeletal isomerization unit configured to receive the bio n-butenes containing stream, convert n-butenes to produce a skeletal isomerization C4 olefin containing stream comprising isobutene and n-butenes; and a catalytic separation unit configured to receive the skeletal isomerization C4 olefin containing stream, convert olefins and/or isoolefins contained therein to produce a converted skeletal isomerization reaction product, and to fractionate the converted skeletal isomerization reaction product to produce a bio isobutene product fraction;

wherein the dimerization unit comprises:

a reaction zone comprising one or more dimerization reactors, each containing an ethylene dimerization catalyst, configured for receiving the bio ethylene containing stream and to convert the bio ethylene to bio n-butenes, producing a dimerization reactor effluent comprising bio n-butenes and C5 and heavier hydrocarbons; and a separation zone configured for receiving the dimerization reactor effluent and for separating the bio n-butenes from the C5 and heavier hydrocarbons, producing the bio n-butenes containing stream and a stream containing the C5 and heavier hydrocarbons.

2. The system of claim 1, wherein the catalytic separation unit comprises a catalytic distillation column configured to receive the skeletal isomerization C4 olefin containing stream, convert 1-butene contained in the n-butenes to 2-butenes, and fractionate isobutene from the 2-butenes to produce a 2-butenes stream and the bio isobutene product fraction.

3. The system of claim 1, wherein the catalytic separation unit comprises an oxygenate reactor configured to react the isobutene with an alcohol or water to produce an alcohol intermediate or an ether intermediate, a separator configured to separate the n-butenes from the alcohol or ether intermediate, a back-cracking reactor configured to convert the alcohol or ether intermediate and produce a reaction effluent comprising the isobutene and the alcohol or water, and a separation system configured to separate the reaction effluent to produce the bio isobutene product fraction.

4. The system of claim 1, wherein the dehydration unit comprises:

a reaction zone comprising one or more dehydration reactors, each containing an ethanol dehydration catalyst, configured for receiving the bio ethanol containing stream and to convert the bio ethanol to bio ethylene, producing a dehydration reactor effluent comprising bio ethylene and water; and a separation zone configured for receiving the dehydration reactor effluent and for separating the bio ethylene from the water, producing the bio ethylene containing stream and a water stream.

5. The system of claim 1, wherein the olefin skeletal isomerization unit comprises:

a reaction zone comprising one or more skeletal isomerization reactors, each containing an olefin skeletal isomerization catalyst, configured for receiving the bio n-butenes containing stream and to convert the bio n-butenes to bio isobutene, producing a skeletal isomerization reactor effluent comprising bio C4 olefins including bio n-butenes and bio isobutene, C3 and lighter hydrocarbons, and C5+ hydrocarbons; and a separation zone configured for receiving the skeletal isomerization reactor effluent and for separating the bio C4 olefins from the C3 and lighter hydrocarbons and the C5 and heavier hydrocarbons, producing the skeletal isomerization C4 olefin containing stream, a C3 and lighter hydrocarbon containing stream, and a C5+ hydrocarbon containing stream.

6. The system of claim 5, wherein the catalytic separation unit comprises a catalytic deisobutenizer unit comprising:

a catalytic distillation reactor, containing a positional isomerization reaction zone and distillation structure, configured for reacting 1-butene contained in the bio n-butenes to 2-butenes and for separating the 2-butenes from bio iso-butene, and to recover a 2-butenes stream and the bio isobutene product fraction.

7. The system of claim 2, comprising a hydrogenation reactor configured to hydrogenate a portion of the 2-butenes in the 2-butenes stream to produce a hydrogenation effluent comprising 2-butenes and n-butane.

8. The system of claim 7, further comprising a flow line for feeding the hydrogenation effluent to the olefin skeletal isomerization unit.

9. The system of claim 1, wherein the bio isobutene product fraction comprises isobutane, the system comprising a splitter for separating at least a portion of the isobutane from the bio isobutene and for recovering a bio isobutane stream and a bio isobutene stream having an enhanced concentration of bio isobutene.

10. A method of producing high purity isobutene from bio ethanol, the method comprising:

dehydrating bio ethanol to produce bio ethylene;

dimerizing the bio ethylene to form bio n-butenes and separating the bio n-butenes from C5 and heavier hydrocarbons;

skeletal isomerizing the bio n-butenes to form a bio C4 mixture comprising isobutene, isobutane, n-butenes, and n-butane;

reacting and fractionating the bio C4 mixture to separate bio isobutene from unconverted n-butenes;

recovering the bio isobutene; and recycling the unconverted n-butenes into the skeletal isomerizing step.

11. The method of claim 10, comprising hydrogenating a portion of the unconverted n-butenes to form a mixture comprising n-butane, and recycling the mixture to the skeletal isomerizing step.

12. The method of claim 10, wherein the dehydrating bio ethanol to produce bio ethylene comprises:

feeding the bio ethanol containing stream to a dehydration reaction zone comprising one or more dehydration reactors, each containing an ethanol dehydration catalyst;

contacting bio ethanol with the ethanol dehydration catalyst at reaction conditions to convert the bio ethanol to bio ethylene;

recovering a dehydration reaction effluent from the dehydration reaction zone, the dehydration reaction effluent comprising the bio ethylene and water; and separating the dehydration reaction effluent to recover a stream comprising the bio ethylene and a water stream.

13. The method of claim 12, wherein the dimerizing the bio ethylene to form bio n-butenes comprises:

feeding the stream comprising the bio ethylene to a dimerization reaction zone comprising one or more dimerization reactors, each containing an ethylene dimerization catalyst;

contacting the bio ethylene with the ethylene dimerization catalyst at reaction conditions to convert the bio ethylene to bio butenes;
recovering a dimerization reaction effluent from the dimerization reaction zone comprising the bio n-butenes, and C5 and heavier reaction byproducts; and
separating the dimerization reaction effluent to recover a stream comprising the bio n-butenes and a stream comprising the C5 and heavier reaction byproducts.

14. The method of claim 13, wherein the skeletal isomerizing the bio n-butenes to form a bio C4 mixture comprises:
feeding the stream comprising the bio n-butenes to a skeletal isomerization reaction zone comprising one or more skeletal isomerization reactors, each containing a skeletal isomerization catalyst;
contacting the bio n-butenes with the skeletal isomerization catalyst at reaction conditions to convert n-butenes to isobutene;
recovering a skeletal isomerization reaction effluent comprising the bio C4 mixture, C3 and lighter reaction byproducts and C5+ reaction byproducts; and
separating the skeletal isomerization reaction effluent to recover a stream comprising the bio C4 mixture, a stream comprising the C3 and lighter reaction byproducts, and a stream comprising the C5+ reaction byproducts.

15. The method of claim 14, wherein the fractionating comprises:
feeding the stream comprising the bio C4 mixture to a catalytic distillation reactor containing a positional isomerization catalyst;
in the catalytic distillation reactor:
converting 1-butene in the bio C4 mixture to 2-butenes;
separating the isobutane and bio isobutene from the 2-butenes and n-butane;
recovering an overhead fraction containing the isobutane and bio isobutene; and
recovering a bottoms fraction containing the 2-butenes and n-butane; and
separating the overhead fraction to recover an isobutane fraction and a bio isobutene fraction having a concentration of bio isobutene of at least 95 wt %.

16. The method of claim 15, comprising recycling the bottoms fraction to the skeletal isomerization reaction zone.

17. The method of claim 16, comprising hydrogenating a portion of the 2-butenes in the bottoms fraction to form additional n-butane prior to recycling the bottoms fraction to the skeletal isomerization reaction zone.

18. A system for converting bio ethanol to high purity bio-isobutene, the system comprising:
a dehydration unit configured to receive a bio ethanol containing stream, convert the bio ethanol to bio ethylene, and produce a bio ethylene containing stream;
a dimerization unit configured to receive the bio ethylene containing stream, dimerize the bio ethylene to produce a dimerization reactor effluent comprising bio n-butenes and C5 or heavier hydrocarbons, separate the bio n-butenes from the dimerization reactor effluent and produce a bio n-butenes containing stream;
an olefin skeletal isomerization unit configured to receive the bio n-butenes containing stream, convert n-butenes to produce a skeletal isomerization C4 olefin containing stream comprising isobutene and n-butenes; and
a catalytic reaction/separation unit configured to:
receive the skeletal isomerization C4 olefin containing stream,
convert isobutene to one or more of methyl tert-butyl ether, ethyl tert-butyl ether, tertiary butyl alcohol and isobutyl alcohol,
separate the n-butenes from the one or more of methyl tert-butyl ether, tertiary butyl alcohol and isobutyl alcohol,
back crack the one or more of methyl tert-butyl ether, tertiary butyl alcohol and isobutyl alcohol to form isobutene and one or more of water and methanol, and
separate the isobutene from the one or more of water and methanol to produce a bio isobutene product fraction; or
a catalytic reaction/separation unit configured to:
receive the skeletal isomerization C4 olefin containing stream;
convert 1-butene contained in the n-butenes to 2-butenes;
separate the 2-butenes from the isobutene to produce a 2-butenes fraction and a bio isobutene product fraction.

19. The system of claim 18, further comprising recovering one or more of a methyl tert-butyl ether product stream, an ethyl tert-butyl ether product stream, and a 1-butene product stream from the catalytic reaction/separation unit.

20. The system of claim 18, wherein the dehydration unit comprises:
a reaction zone comprising one or more dehydration reactors, each containing an ethanol dehydration catalyst, configured for receiving the bio ethanol containing stream and to convert the bio ethanol to bio ethylene, producing a dehydration reactor effluent comprising bio ethylene and water; and
a separation zone configured for receiving the dehydration reactor effluent and for separating the bio ethylene from the water, producing the bio ethylene containing stream and a water stream.

21. The system of claim 20, wherein the dimerization unit comprises:
a reaction zone comprising one or more dimerization reactors, each containing an ethylene dimerization catalyst, configured for receiving the bio ethylene containing stream and to convert the bio ethylene to bio n-butenes, producing a dimerization reactor effluent comprising bio n-butenes and C5 and heavier hydrocarbons; and
a separation zone configured for receiving the dimerization reactor effluent and for separating the bio n-butenes from the C5 and heavier hydrocarbons, producing the bio n-butenes containing stream and a stream containing the C5 and heavier hydrocarbons.

22. The system of claim 21, wherein the olefin skeletal isomerization unit comprises:
a reaction zone comprising one or more skeletal isomerization reactors, each containing an olefin skeletal isomerization catalyst, configured for receiving the bio n-butenes containing stream and to convert the bio n-butenes to bio isobutene, producing a skeletal isomerization reactor effluent comprising bio C4 olefins including bio n-butenes and bio isobutene, C3 and lighter hydrocarbons, and C5+ hydrocarbons; and
a separation zone configured for receiving the skeletal isomerization reactor effluent and for separating the bio C4 olefins from the C3 and lighter hydrocarbons and the C5 and heavier hydrocarbons, producing the skeletal isomerization C4 olefin containing stream, a C3 and lighter hydrocarbon containing stream, and a C5+ hydrocarbon containing stream.

* * * * *